(12) United States Patent
Nestler et al.

(10) Patent No.: US 6,555,707 B1
(45) Date of Patent: Apr. 29, 2003

(54) METHOD FOR PRODUCING ACRYLIC ACID AND ACRYLIC ACIDS ESTERS

(75) Inventors: Gerhard Nestler, Ludwigshafen (DE); Jürgen Schröder, Ludwigshafen (DE); Gerhard Bolz, Frankenthal (DE)

(73) Assignee: BASF Aktiengesellschaft, Ludwigshaften (DE)

( * ) Notice: Subject to any disclaimer, the term of this patent is extended or adjusted under 35 U.S.C. 154(b) by 0 days.

(21) Appl. No.: 09/646,751

(22) PCT Filed: Mar. 24, 1999

(86) PCT No.: PCT/EP99/01998

§ 371 (c)(1),
(2), (4) Date: Sep. 22, 2000

(87) PCT Pub. No.: WO99/50220

PCT Pub. Date: Oct. 7, 1999

(30) Foreign Application Priority Data

Mar. 31, 1998 (DE) .......................... 198 14 375

(51) Int. Cl.⁷ .............................. C07C 51/16
(52) U.S. Cl. ............... 562/545; 560/208; 562/546; 562/547; 562/600
(58) Field of Search ................ 562/600, 532, 562/538, 545, 546, 547; 560/208

(56) References Cited

U.S. PATENT DOCUMENTS

| | | | |
|---|---|---|---|
| 3,555,082 A | | 1/1971 | Sennewald et al. |
| 3,844,903 A | | 10/1974 | Willersinn et al. |
| 4,999,452 A | * | 3/1991 | Bunning et al. |
| 5,154,800 A | | 10/1992 | Berg |
| 5,817,865 A | * | 10/1998 | Machhammer et al. |

FOREIGN PATENT DOCUMENTS

| | | |
|---|---|---|
| DE | 2 035 228 | 1/1971 |
| DE | 1 668 362 | 8/1971 |
| DE | 2 1 64 767 | 7/1972 |
| DE | 2 136 396 | 2/1973 |
| DE | 34 29 391 | 2/1985 |
| DE | 2 1 21 123 | 11/1992 |
| DE | 43 08 987 | 9/1994 |
| DE | 197 40 253 | 3/1999 |
| DE | 19740253 A1 * | 3/1999 |
| EP | 0 009 545 | 4/1980 |
| EP | 0 398 226 | 11/1990 |
| FR | 1 452 566 | 9/1966 |

OTHER PUBLICATIONS

English translation of DE–19740253.*

* cited by examiner

Primary Examiner—Michael L. Shippen
(74) Attorney, Agent, or Firm—Oblon, Spivak, McClelland, Maier & Neustadt, P.C.

(57) ABSTRACT

A process for preparing acrylic acid and/or acrylates, which comprises stage A with or without stages B and C:

A: cooling a gaseous reaction mixture which comprises acrylic acid and is obtained in the gas-phase oxidation to prepare acrylic acid, using an inert high-boiling solvent, to give a gaseous mixture comprising acrylic acid;

B: separating the gaseous mixture comprising acrylic acid to give a low-boiling fraction, a crude acrylic acid, and a bottom product, and C: esterifying the crude acrylic acid obtained in stage B by means of one or more alkanols to give an esterification mixture comprising one or more acrylates and one or more acetic esters.

20 Claims, 1 Drawing Sheet

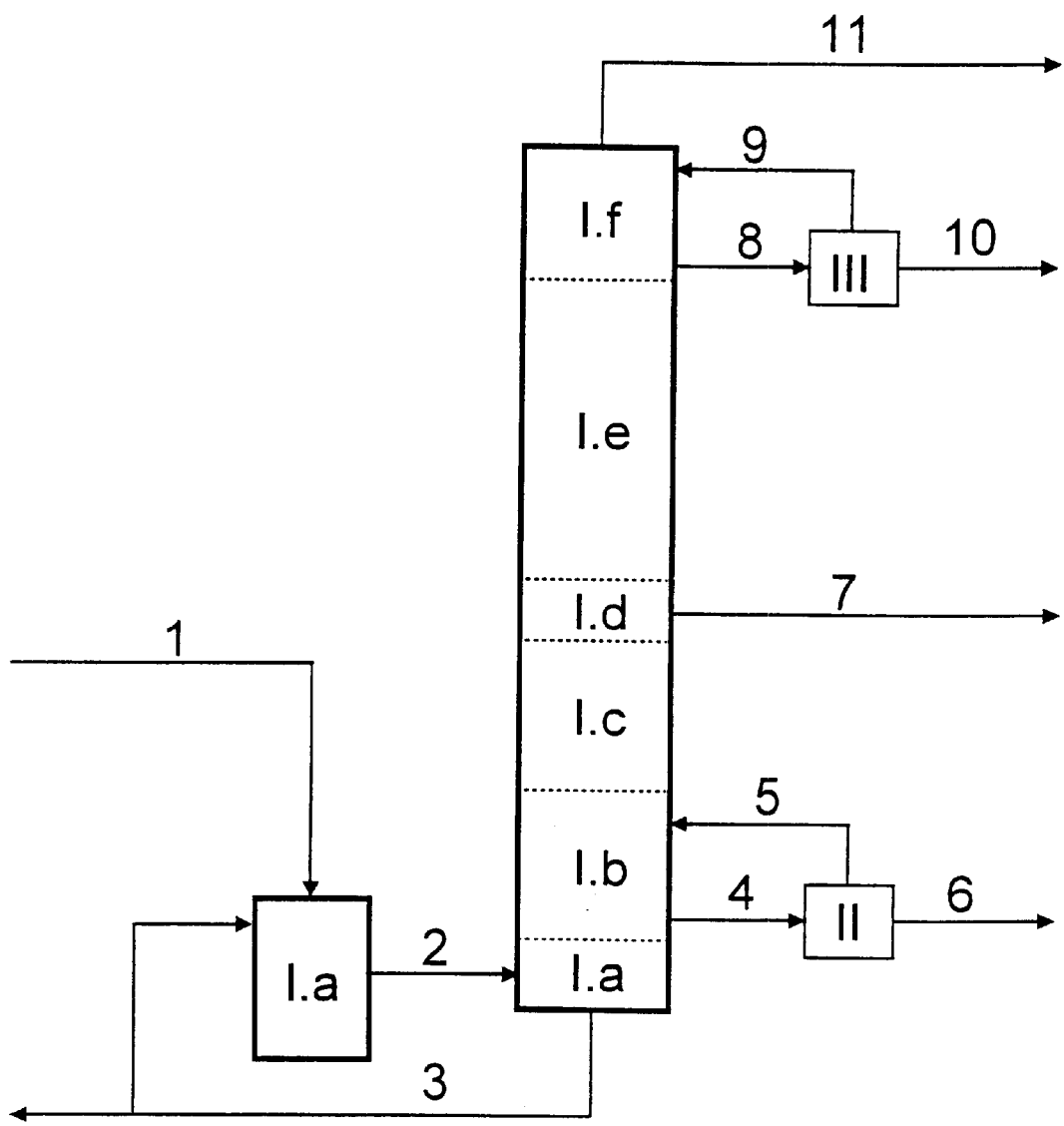

METHOD FOR PRODUCING ACRYLIC ACID AND ACRYLIC ACIDS ESTERS

The present invention relates to a process for preparing acrylic acid that involves using an inert high-boiling solvent to cool a gaseous reaction mixture which comprises acrylic acid and is obtained in the gas-phase oxidation to prepare acrylic acid and that produces a gaseous mixture comprising acrylic acid. Moreover it relates very generally to the use of an inert high-boiling solvent to cool a gaseous reaction mixture produced in the gas-phase oxidation to prepare acrylic acid, and to a process for preparing acrylates.

Because of its highly reactive double bond and the acid function, acrylic acid is a valuable monomer for preparing addition polymers, for example, for aqueous polymer dispersions suitable as adhesives.

One route to acrylic acid is the gas-phase oxidation of propylene and/or acrolein with oxygen or gases comprising oxygen in the presence of catalysts at elevated temperature preferably with dilution of the reactants with inert gases and/or steam owing to the high heat of reaction.

Catalysts employed in this oxidation are generally multicomponent oxide-type systems based, for example, on oxides of molybdenum, of chromium, of vanadium or of tellurium.

However, this process leads not to pure acrylic acid but rather to a gas mixture which in addition to acrylic acid comprises secondary components—mainly unreacted acrolein and/or propylene, steam, oxides of carbon, nitrogen, oxygen, acetic acid, formaldehyde, benzaldehyde, furfurals, and maleic anhydride. The acrylic acid has to be separated from this gas mixture subsequently.

Isolation of the acrylic acid from the gaseous reaction mixture is generally carried out by countercurrent absorption using, for example, a high-boiling solvent or solvent mixture and a plurality of subsequent distillative processing steps, as is described, for example, in DE-A 21 36 396 and DE-A 43 08 087. In EP-B 0 009 545, U.S. Pat. No. 5,154,800, DE-A 34 29 391 and DE-A 21 21 123 absorption takes place first with water/aqueous acrylic acid in countercurrent and is followed by extractive or azeotropic distillation.

A disadvantage with these processes is that the organic solvent/solvent mixture used for the absorption and, where appropriate, extraction must be separated off again in a separate distillation step and possibly purified before being used again.

A further disadvantage of these processes is that the acetic acid produced in the acrylic acid preparation (purity: 0.5 to 10% by weight relative to the amount of acrylic acid) has to be separated off in a complex distillation stage. Because of the small differences in boiling point and the great tendency of acrylic acid to polymerize, this stage generally involves a number of distillation steps. as can be seen, inter alia, from U.S. Pat. No. 3,844,903, and is the cause of considerable losses of acrylic acid (cf. EP-A 398 226).

In view of the known fact that acrylic compounds have a high tendency to undergo addition polymerization, processes operating with multistage distillative workup are disadvantageous in very general terms since they heighten the polymerization tendency of the acrylic acid.

Also known from the prior art is the preparation of acrylates by acid-catalyzed esterification of acrylic acid with one or more alkanols. In very general terms it is known of such esterification reactions that they are equilibrium reactions and thus that the presence of water in the reaction equilibrium prevents economic conversion rates. Accordingly, the acrylic acid employed in general is substantially anhydrous and the water of reaction formed during the esterification is removed by distillation with the aid, if desired, of an entrainer.

As already mentioned earlier, the oxidative preparation of acrylic acid starting from the corresponding $C_3$ precursors also produces considerable amounts of acetic acid (0.5 to 10% by weight). Because of the in some instances small differences in boiling point and high polymerization tendency of acrylic acid when exposed to heat the distillative separation of the abovementioned byproducts is difficult and laborious (U.S. Pat. No. 3,844,903, DE-A 2 164 767).

In the esterification of acrylic acid, containing acetic acid, with alkanols the acetic acid too is esterified; the formation of the acetic ester entails additional separation effort and a loss of alkanol. A further point to note is that the distillative separation of the alkyl acetate from the esterification mixture, and especially the separation of unreacted alkanol, is hindered by the formation of binary azeotropes.

In the case of, say, butanol, the butanol/butyl acetate azeotrope boils at 115.8° C. (57% butanol); butanol boils at 117.4° C. and butyl acetate at 125.6° C.

Since the acetic esters are quite highly volatile and are not polymerizable, high-purity acrylates are generally required for the preparation of polymers; that is, acrylates which are as far as possible free—i.e., essentially free—from acetic esters. Indeed, one of the consequences of the residual acetic ester in a coating dispersion or in an adhesive, for example, would be severe odor nuisance. Laborious removal (deodorization) of the acetic ester would be necessary.

As emerges from the above there is a fundamental problem in acrylate preparation of excessive consumption of alkanols, which is disadvantageous from both an economic and an environmental standpoint.

Various attempts have therefore been made in the past to solve the problems caused in esterification with alkanols by the byproducts, such as acetic acid and water, that are produced during the synthesis of acrylic acid by gas-phase oxidation.

For instance, DE-A 20 35 228 describes the esterification of aqueous acrylic acid (water content at least 30%) in the presence of acidic catalysts, such as sulfuric, sulfonic and/or phosphoric acid, and an organic solvent mixture.

This process is particularly disadvantageous in that, owing to the large amount of water and the consequent reduction in catalyst concentration, a large amount of catalyst has to be used. In order to obtain useful conversion rates and rates of esterification, moreover, said document requires the use of specific solvent mixtures consisting of an aromatic and an aliphatic hydrocarbon. A further condition for successful implementation of this process is that the solvent mixture must also have a significantly higher boiling point than the acrylate.

EP-A 0 398 226 proposes partial condensation of the reaction gases from the propylene oxidation and direct esterification of the resultant "enriched" acrylic acid, with the acrylic acid remaining in the reaction gas being conventionally extracted by scrubbing with water and separated off by distillation. This process of two-stage acrylic acid condensation is highly laborious and does not produce acrylic acid which is free from, or even low in, acetic acid. As shown by the examples reproduced therein, the esterification mixtures that are obtained still contain from 1.8 to 2.5% by weight of acetic ester.

In DE-A 16 68 362 the acrylic acid-containing reaction gas from the oxidation of propylene is treated with the mixture of high boilers obtained in the course of the esterification, consisting essentially of maleic esters, polyacrylic acid and polyacrylic esters, and the acrylic acid solution obtained in this treatment is freed-from the low boilers by distillation. The solution thus obtained at the bottom of the distillation column, which includes acrylic acid, is esterified with alkanols in the presence of acidic cation exchangers.

A disadvantage of this process is that the workup of acrylic acid is coupled to the ester preparation, and the option of preparing different esters is lost. Furthermore, the formation of high-boiling esters of polyacrylic acid, the excess of which has to be removed, entails considerable losses of alkanol.

JA 7 014 529-R describes the preparation of butyl acrylate from aqueous acrylic acid. According to the process described in said document acrylic acid is extracted from the aqueous solution with a butyl acrylate/butanol mixture and then the extract, which contains about 18% by weight acrylic acid, about 1% by weight acetic acid and about 11% by weight water, is esterified vbith an alcohol.

The primary disadvantage of this process is that large quantities of water and acetic acid are carried into the esterification, which has an adverse effect on the esterification, disrupts the workup of the esterification mixture, and results in alkanol losses.

FR-B 1 452 566 relates to the extraction of acrylic acid from an aqueous solution with acetophenone or tributyl phosphate and the esterification of this acrylic acid with excess alcohol in the presence of an extractant. The yield of acrylate in this process, however, is less than 80% relative to the acrylic acid present in the starting solution.

Because of the adverse effect of the presence of significant amounts of water and acetic acid on the preparation of acrylates, the acrylic acid used to prepare acrylates is generally anhydrous and purified, containing only traces of acetic acid.

It is an object of the present invention to provide a simple process for obtaining crude acrylic acid of low water content, which can be carried out in an energetically favorable manner.

It is a further object of the present invention to provide a technically simple and economic process for preparing acrylates, in which the losses of alkanol are low despite the presence of acetic acid in the acrylic acid employed.

We have found that these objects are achieved by the present invention, which provides a process for preparing acrylic acid comprising the following stage A:

A: cooling a gaseous reaction mixture which comprises acrylic acid and is obtained in the gas-phase oxidation to prepare acrylic acid, using an inert high-boiling solvent, to give a gaseous mixture comprising acrylic acid.

The term "gaseous reaction mixture which comprises acrylic acid" embraces, for the purposes of the invention, all reaction mixtures obtained in the gas-phase oxidation to prepare acrylic acid.

The preparation of acrylic acid takes place here conventionally over multicomponent oxide-type catalysts at approximately 200 to 400° C. Although in principle all known reactor types can be used, it is preferred to employ tube bundle heat exchangers that are packed with the oxidation catalyst. The reason for this is that the major proportion of the heat liberated in the course of the oxidation can be dissipated by convection and radiation to the cooled tube walls.

If propylene/acrolein are used as starting materials to prepare acrylic acid, the gaseous reaction mixture concerned is obtained at a temperature of approximately 200 to 300° C. from the gas-phase oxidation and comprises from about 1 to about 30% by weight of acrylic acid with the following byproducts: unreacted propylene (from about 0.05 to about 1% by weight), acrolein (from about 0.001 to about 2% by weight), propane (from about 0.01 to about 2% by weight), steam (from about 1 to about 30% by weight), oxides of carbon (from about 0.05 to about 15% by weight), nitrogen (from 0 to about 90% by weight), oxygen (from about 0.05 to about 10% by weight), acetic acid (from about 0.05 to about 2% by weight), propionic acid (from about 0.01 to about 2% by weight), aldehydes (from about 0.05 to about 3% by weight), and maleic anhydride (from about 0.01 to about 0.5% by weight).

This gaseous reaction mixture is cooled by means of an inert high-boiling solvent, generally to a temperature from approximately 100 to approximately 190° C., preferably from approximately 120 to approximately 180° C. and, in particular, from approximately 130 to approximately 160° C. to give a further gaseous mixture comprising acrylic acid.

The term "inert high-boiling solvent" embraces liquids whose boiling point is above that of acrylic acid, preferably above 160° C. at 1 atm pressure. As examples of such solvents mention may be made, for example, of biphenyl, diphenyl ether, dimethyl phthalate, ethylhexanoic acid, N-methylpyrrolidone, and fractions from the distillation of paraffin, or mixtures of two or more of these solvents.

Preferably, the inert high-boiling solvent used for cooling is circulated and in particular, for the purpose of heat dissipation, is circulated via a conventional heat exchanger.

It is preferred to add stabilizers, such as phenothiazine, hydroquinone, a phenolic compound, or a mixture of two or more of these stabilizers, to said solvent, the concentration of the stabilizer being from 0.01 to 1% by weight. Stabilizers preferably employed are phenothiazine, hydroquinone or a mixture of phenothiazine and an N—O compound, such as p-nitrosophenol, p-nitrosodiethylaniline or a tetramethylpiperidine-1-oxyl.

As the cooling apparatus it is possible to use any prior art apparatus known for this purpose, with preference being given to the use of Venturi scrubbers or spray coolers (quench), especially the latter.

The resultant gaseous mixture comprising acrylic acid is preferably separated in a stage B to give a low-boiling fraction, a crude acrylic acid and a bottom product. Separation in accordance with stage B is conducted in particular in a distillation column. In that case the cooled gaseous mixture comprising acrylic acid is passed into the bottom part of the distillation column and the distillation is conducted such that the gaseous constituents and the low boilers, i.e., principally acetic acid and water, are separated off via the top of the column.

The acrylic acid present is taken off as crude acrylic acid by way of a sidestream takeoff of the column. The high boilers, such as oligomeric acrylic acid, for example, are obtained in the bottom of the column. The crude acrylic acid obtained in this way generally contains from about 0.1 to about 2% by weight acetic acid and from about 0.5 to about 3% water. The bottom product also includes further high boilers, such as residues of the inert high boiling solvent, and stabilizers.

The procedure here is generally as follows:

The gaseous mixture from stage A, comprising acrylic acid, is passed into the bottom part of a distillation column in which the gaseous constituents and the low boilers, especially aldehydes, acetic acid and water, are separated off via the top of the column.

The acrylic acid is drawn off as crude acrylic acid in the bottom third of the distillation column via a sidestream takeoff.

The high boilers, principally the inert high-boiling solvent and oligomeric acrylic acid, are obtained in the bottom (liquid phase) of the distillation column.

The distillation columns (columns) which can be employed for the process of the invention are not subject to any particular restriction. In principle, suitable columns are all those having internals which provide for effective separation.

Suitable column internals are all customary internals, especially trays, and random and/or structured packings. Of the trays, preference is given to bubble-cap trays, sieve trays, valve trays and/or dual-flow trays.

The column comprises at least one cooling apparatus. Suitable such apparatus comprises all those heat transfer devices or heat exchangers where the heat liberated during the condensation is dissipated indirectly (externally). All customary apparatuses can be employed for this purpose, with preference being given to tube bundle heat exchangers, plate heat exchangers and air coolers. Suitable cooling media are, in the case of an air cooler, appropriately, air, and in the case of other cooling apparatuses liquid coolants, especially water. Where only one cooling apparatus is provided it is installed at the top of the column, where the low-boiling fraction is condensed out.

The skilled worker will readily be able to determine the number of cooling apparatuses required as a function of the desired purity of the condensed fractions and thus of the components, the purity of the condensed components being determined essentially by the installed separation efficiency of the column, i.e., the column height, the number of trays and the energy introduced by the gaseous mixture from stage A that is to be condensed. Judiciously, when two or more cooling apparatuses are present, they are installed in different sections of the column.

In the case, for example, of a gaseous mixture from stage A which comprises not only the high proportion of uncondensable components but also a high-boiling, middle-boiling and low-boiling fraction, one cooling apparatus may be provided in the bottom section of the column to condense out the high-boiling fraction and one cooling apparatus may be provided at the top of the column to condense out the low-boiling fraction. The condensed fractions are led off by way of sidestream takeoffs at the respective sections in the column. Depending on the number of components in the high-boiling, middle-boiling and lowboiling fraction it is possible in each case to provide two or more sidestream takeoffs. The fractions drawn off by way of the sidestream takeoffs can then be subjected to further purification stages, examples being distillative or extractive separation procedures or a crystallization, depending on the desired purity of the components.

In a preferred embodiment of the invention one takeoff for high boilers, one takeoff for low boilers and 1 or 2 takeoffs for middle boilers are provided.

The pressure within the column depends on the amount of uncondensable components and is preferably 0.5–5 bar absolute, especially 0.8–3 bar absolute.

The temperature in the region of the separating device in which the low boilers—that is, essentially and typically, aldehydes, acetic acid and water—are separated off is from approximately 25 to approximately 50° C., preferably from approximately 30 to approximately 40° C.; the temperature in the region in which the crude acrylic acid is obtained is from approximately 70 to 110° C., preferably from approximately 80 to 100° C. The bottom temperature is maintained at from approximately 90 to approximately 140° C., in particular at from approximately 115 to 135° C.

The precise operating conditions for the column, such as temperature and pressure regime, arrangement and positioning of the cooling apparatus(es), positioning of the sidestream takeoffs for drawing off the desired fractions, choice of column height and column diameter, number and spacing of the separation-effective internals/trays in the column, and the nature of the separation-effective column internals, can be determined by the skilled worker in dependence on the particular separation task within the scope of experiments that are customary in the art.

In the presence of a high-boiling fraction, a middle-boiling fraction, a low-boiling fraction and uncondensable component(s) in the gaseous mixture comprising acrylic acid (gaseous mixture), the process is advantageously conducted as shown in the Figure and as described below, the column being subdivisible into different sections in which different technical processing problems are solved.

The reference characters in the Figure in this case denote the individual sections in the column (I.a to I.f) and separate sections/apparatuses upstream of the column (E), incoming and outgoing lines (1–12), and the cooling circuits II and III.

E. Quench:
  Cooling the gaseous mixture
    In the installation E the gaseous mixture is introduced and cooled. This can be done by indirect cooling, with an inert high-boiling solvent (LM) as the cooling medium, which can be supplied via line (12). In this case the gaseous mixture from line 1 is cooled in a quench E and is supplied via line 2 to the bottom region I.a of the column. By way of line 3, the condensed high-boiling fraction is mixed together with the inert high-boiling solvent and is supplied to the cooling circuit and passed back into the quench. Here, the mixture of high-boiling fraction and inert highboiling solvent that is passed back for cooling can be cooled in a cooler (K), preferably to 80–150° C. A fraction of the stream, usually from 0.1 to 10% by weight based on 100% by weight of the acrylic acid obtained, is removed from the process and partly replaced by fresh solvent by way of line 12.

I.b Cooling circuit II:
  Condensing the high-boiling fraction
    In the column section I.b, the heat of condensation is dissipated externally by way of cooling circuit II, by means of a heat exchanger with, for example, water as the cooling medium, by taking off condensed high-boiling fraction from the column by way of line 4, cooling it and recycling one portion of the cooled, condensed highboiling fraction to the column via line 5, while another portion, corresponding to the level in the quench, is removed by way of line 3 or passed back into the quench E.

I.c Cooling circuit II→sidestream takeoff:
  Concentrating high boilers
    In the column section I.c between column section I.b (cooling circuit II) and I.d (sidestream takeoff), toward the cooling circuit II, the high-boiling fraction is concentrated by distillation and condensed out from the gaseous mixture that is passed upward in countercurrent.

I.d Sidestream takeoff:
  Drawing off the middle-boiling fraction
    By way of sidestream takeoff 7 in the column section I.d the desired target component, acrylic acid, is taken off in liquid form as crude acrylic acid by way, for example, of a catchplate and some of it is passed as a reflux (R) below the sidestream takeoff 7 through a heat exchanger (WT) and back into the column.

I.e Sidestream takeoff cooling circuit III:
Concentrating the middle boilers
In the column section I.e between column section I.d (sidestream takeoff 7) and I.f (cooling circuit III), the middle-boiling fraction of the gaseous mixture is concentrated by distillation from the gaseous mixture passed upward, the middleboiling fraction being concentrated toward the sidestream takeoff (region I.d).

I.f Cooling circuit III:
Condensing the low-boiling fraction
In the column section I.f of the external cooling circuit III, the low-boiling fraction is condensed from the gaseous mixture passed upward in countercurrent. As with the cooling circuit II, the heat of condensation is dissipated externally by way of cooling circuit III by means of a heat exchanger (not shown) with, for example, water as the cooling medium by drawing off condensed low-boiling fraction by way of line 8, cooling it and recycling one portion of the cooled, condensed lowboiling fraction to the column via line 9, while the other portion is removed via line 10. The uncondensed gases are drawn off from the top of the column via line 11, it also being possible if appropriate to superheat the gas stream in order to prevent further condensation in the vapor pipe.

The gas is preferably passed back via line 11 as circulation gas into the acrylic acid preparation stage.

Further details regarding this procedure are given in DE-A 197 40 253, the content of which is included in its entirety in the context of the present application by reference. During the separation procedure a polymerization inhibitor is added for stabilization, such as phenothiazine, a phenolic compound, an N—O compound or a mixture of two or more of these compounds, preferably phenothiazine or hydroquinone, a mixture of phenothiazine and hydroquinone, hydroquinone monomethyl ether, p-nitrosophenol, nitrosodiethylaniline or tetramethylpiperidine-1-oxyls, as are described in DE-A-16 18 141.

The low boilers obtained after the separation, i.e. essentially water and acetic acid, are removed from the separating apparatus and then passed back in whole or in part, with or without the addition of a polymerization inhibitor, as a reflux back into the upper part of the separation apparatus in order therein to facilitate the condensation of the low boilers contained in the gaseous mixture comprising acrylic acid.

The crude acrylic acid obtained as a middle boiler, preferably via a sidestream takeoff, is subjected in whole or in part to crystallization or distillation by a prior art technique to give a pure acrylic acid. In this case, mother liquor from the crystallization, in whole or in part, and/or a portion of the crude acrylic acid, is supplied to the column below the sidestream takeoff.

Furthermore, the crude acrylic acid obtained in accordance with the invention can also be subjected to esterification with an alkanol.

The present invention therefore additionally provides a process for preparing an acrylate, or a mixture of two or more thereof, which in addition to the above-defined stages A and B comprises a further stage C:

C: esterifying the crude acrylic acid obtained in stage B by means of one or more alkanols to give an esterification mixture comprising one or more acrylates and one or more acetic esters.

Further details regarding the esterification of acrylic acid can be found in DE-A 195 47 485 and the prior art cited therein, the content of which is incorporated in its entirety by reference in the context of the present application.

The invention also provides a process which in addition to stages A to C comprises a further stage D:

D: separating the esterification mixture to give one or more acrylates and a separation mixture which comprises one or more acetic esters.

In one preferred embodiment the process of the invention for preparing acrylic acid is conducted as follows.

The crude acrylic acid is esterified directly with a $C_1$–$C_{12}$-, preferably a $C_1$–$C_{10}$- and, in particular, a $C_4$–$C_8$-alkanol. Said esterification is carried out in accordance with a prior art process, an example being the process of DE-A 195 47 485, with the esterification conditions being dependent on the alkanol used.

Preferred alkanols are:
methanol, ethanol, isopropanol, n-butanol, isobutanol, octanol, 2-ethylhexanol, preferably n-butanol, isobutanol and 2-ethylhexanol.

Typical conditions under which the esterification can take place are as follows:
Ratio alkanol:acrylic acid:
1:0.7–1.2 (molar)
Catalyst:
sulfuric acid or a sulfonic acid, such as p-toluenesulfonic acid
Amount of catalyst:
approximately 0.1–10% by weight, preferably approximately 0.5–5% by weight, in each case based on the starting materials
Stabilizer:
phenothiazine, hydroquinone, hydroquinone monomethyl ether, phenylenediamine and, if desired, air
Amount of stabilizer:
from approximately 100 to approximately 50,000 ppm, preferably from approximately 500 to approximately 2000 ppm, based in each case on acrylic acid
Reaction temperature:
approximately 80–160° C., preferably approximately 90–130° C.
Pressure during the reaction:
0.5–1.5 bar, preferably atmospheric pressure
Reaction period:
from approximately 1 to approximately 10 hours, preferably from approximately 1 to 6 hours.

If desired it is possible to employ an entrainer, such as cyclohexane or toluene, for removing the water which forms during the esterification.

The esterification per se can be carried out at atmospheric, subatmospheric or superatmospheric pressure and either continuously or batchwise, with preference being given to a continuous regime for the overall process—that is, continuous implementation of said stages A to D.

Since in accordance with the invention the crude acrylic acid obtained in stage B is esterified, the product is an esterification mixture comprising the desired acrylate(s) and, in addition, the corresponding acetic ester(s).

The acrylates are isolated conventionally. In general, first the catalyst and the unreacted acrylic acid are removed by washing and then the esterification mixture is separated, preferably by distillative means.

Said separation produces firstly the one or more acrylates and secondly a separation mixture comprising one or more acetic esters. This separation mixture is preferably hydrolyzed in a further stage E to give a hydrolysis mixture comprising one or more alkanols and acetic salts. The alkanol, in turn, can subsequently be separated off from this hydrolysis mixture.

The procedure here in detail is preferably as follows:

First of all the esterification mixture is separated by distillative means to give a low-boiling fraction which comprises, inter alia, the acetic ester, and a bottom product which comprises the major amount of the acrylate. Subsequently, the bottom product is likewise separated by distillation to give the acrylate via the top of the column.

The low-boiling fraction obtained in the distillative separation, which consists predominantly of alkanol (from approximately 20 to approximately 70%), acetic ester (from approximately 5 to approximately 40%) and acrylate (from approximately 5 to approximately 50%), is treated, alone or together with the distillation bottom product obtained in the pure distillation of the desired ester and comprising, inter alia, diacrylates, alkoxypropionic esters and oligomeric and polymeric acrylates, with an aqueous alkali metal hydroxide solution, preferably NaOH, with a strength of from 5 to 40% by weight, at boiling temperature for from about 30 minutes to about 10 hours.

Here, the low-boiling fraction can if desired be separated in a further separation step, preferably by distillation, into a top product, consisting predominantly of alkanol and acetate, and a bottom product which consists essentially of acrylate. The top product obtained in this case is then hydrolyzed as set out above. The acrylate obtained is preferably supplied to the distillative workup of the esterification mixture.

The reaction with alkali metal hydroxide solution (hydrolysis) can be carried out continuously or batchwise, under atmospheric, superatmospheric or subatmospheric pressure. It is preferably carried out using a stirred reactor or a tube reactor.

The separation of the alkanol from the hydrolysis mixture that is obtained depends on the nature of the alkanol; that is, on its solubility in water. Water-insoluble alkanols form a second phase and can be separated off with ease. Water-soluble alkanols are separated off, for example, by distillation or by stripping with air or steam. Preferably, the alkanols obtained are then supplied to the esterification. Distillative separation or stripping can take place, for example, in a heatable stirred reactor with a column mounted on it. The energy can be supplied conventionally 0acket heating, coil heating, circulation heating, etc.).

The stripping of the alkanol in a stripping column can also take place conventionally. For example, the hot (from approximately 40 to approximately 80° C.) hydrolysis solution can be fed in at the top of the column and stripped in countercurrent with air (from approximately 1 to approximately 20 m$^3$/m$^3$) or steam (from approximately 0.1 to approximately 10 t/m$^3$). The alkanol can be condensed from the stripping gas with a conventional condenser, such as a tube bundle heat exchanger or plate-type heat exchanger.

The alkanol can then be resupplied to the esterification of stage C.

The process of the invention has the following advantages:

1. Crude acrylic acid of low water content can be obtained with technical simplicity. Only one separation apparatus is required, preferably a distillation column.

2. Owing to low polymer contamination, the plant used has a long run time.

3. Owing to the recovery of the alkanol component from the acetic esters obtained in the esterification, losses of alkanol are restricted to a minimum.

In its most general embodiment the present invention provides, moreover, for the use of an inert high-boiling solvent to cool a gaseous reaction mixture comprising acrylic acid and obtained in the gas-phase oxidation to prepare acrylic acid.

The present invention will now be elucidated with reference to an example.

EXAMPLE

Two-stage catalytic oxidation of propylene with molecular oxygen gave, in conventional manner, a gaseous reaction mixture having the following composition:

9.84% by weight acrylic acid, 0.4% by weight acetic acid, 4.42% by weight water, 0.11% by weight acrolein, 0.21% by weight formaldehyde, 0.07% by weight maleic anhydride, and also propionic acid, furfural, propane, propene, nitrogen, oxygen and carbon oxides.

This gaseous reaction mixture was cooled to 140° C. in a spray cooler (quench) by spraying in a eutectic mixture of biphenyl and diphenyl ether (0.5 m$^3$/m$^3$). During this procedure, the crude acrylic acid was circulated via a heat exchanger, and a temperature of 95° C. was established.

The cooled, gaseous mixture comprising acrylic acid was passed via a droplet separator (cyclone) into the bottom part of a distillation column which was equipped with 60 dual-flow trays, a sidestream takeoff between trays 15 and 16, and a spray condenser at the top of the column. The temperature at the top of the distillation column was 34° C., the bottom temperature of the distillation column 118° C.

The distillate obtained in the spray condenser, which consisted predominantly of water and acetic acid, underwent removal of 20% of itself, had 500 ppm of hydroquinone added, and then was applied again as a reflux to the topmost column tray.

The bottom (liquid phase) of the distillation column was passed back to column tray 5 via a heat exchanger, which established a temperature of 95° C.

The crude acrylic acid removed via the sidestream takeoff contained 96.6% by weight acrylic acid, 1.2% by weight acetic acid, 0.05% by weight propionic acid and 1.5% by weight water.

100 ml of crude acrylic acid stabilized with 2000 ppm of phenothiazine were metered in hourly to tray 20.

A cascade of stirred vessels, consisting of three stirred reactors each having a reaction volume of one liter and equipped with column, condenser and phase separation vessel, was charged with 500 g of the crude acrylic acid discharged from the quench, 570 g of butanol and 13 g of sulfuric acid per hour. The reaction temperature in the reactors was 106° C., 118° C. and 123° C.; the pressure was 700 mbar in each case. At the top of the column a mixture of water, butanol and butyl acrylate was obtained which separated into an aqueous and an organic phase. 300 ppm of phenothiazine were added to the organic phase, which was then passed as a reflux to the column.

The reactor discharge (945 g/h) was cooled to 30° C., the unreacted acrylic acid and the catalyst were neutralized with 5% strength sodium hydroxide solution, washing was carried out with water, and then the mixture was distilled in a column having 60 sieve trays. The column was fed at tray 5. The bottom temperature was 110° C., the column-top temperature 88° C., and the pressure 160 mbar.

850 g/h were obtained at the top of this column of a distillate which separated into an organic phase (841 g/h) and a water phase. 300 ppm of phenothiazine were added to 748 g/h of the organic phase, which was then applied as reflux to the top tray of the sieve-tray column again.

The organic phase of the distillate contained 12.3% butyl acetate, 41.7% butanol and 43.6% butyl acrylate.

The product run off from the bottom of the column was separated, in a further sieve-tray column (30 trays), into butyl acrylate with a purity of 99.7% (735 g/h), as column-top product, and high boilers, containing predominantly inhibitors and oligomeric/polymeric butyl acrylate, as bottom product. In this separation, the bottom temperature was 108° C., the column-top temperature 80° C., at a pressure of 100 mbar. The reflux ratio was 0.6.

A mixture of 1,000 g of the organic phase of the distillate was heated under reflux with 40% strength sodium hydroxide solution (800 g) for two hours in a stirred reactor. After the end of the hydrolysis reaction the butanol formed was separated off from the reactor by distillation via a column (10 bubble-cap trays) under subatmospheric pressure (500 mbar). The condensate separated into a water phase and a butanol phase (812 g). The butanol phase was passed back directly to the esterification. In this way it was possible to recover approximately 94% of the theoretical amount of butanol.

We claim:

1. A process comprising:
   obtaining an acrylic acid gaseous reaction mixture by gas-phase oxidation;
   cooling said mixture in the presence of an inert high-boiling solvent; and
   separating said mixture to provide a low-boiling fraction, a crude acrylic acid fraction, and a bottoms product.

2. The process as claimed in claim 1, wherein the separation of stage B is conducted in a distillation column and the crude acrylic acid is obtained via a sidestream takeoff of the distillation column.

3. The process according to claim 1, further comprising converting said crude acrylic acid to pure acrylic acid.

4. A process for preparing an acrylate, or a mixture of two or more thereof, which comprises:
   A: cooling a gaseous reaction mixture which comprises acrylic acid and is obtained in the gas-phase oxidation to prepare acrylic acid, using an inert high-boiling solvent, to give a gaseous mixture comprising acrylic acid;
   B: separating the gaseous mixture comprising acrylic acid to give a low-boiling fraction, a crude acrylic acid, and a bottom product; and
   C: esterifying the crude acrylic acid obtained in stage B by means of one or more alkanols to give an esterification mixture comprising one or more acrylates and one or more acetic esters.

5. The process as claimed in claim 4, further comprising stage D:
   D: separating the esterification mixture to give one or more acrylates and a separation mixture which comprises one or more acetic esters.

6. The process as claimed in claim 5, further comprising stage E:
   E: hydrolyzing the separation mixture to give a hydrolysis mixture which comprises one or more alkanols and acetic salts.

7. The process as claimed in claim 6, wherein one or more alkanols are separated from the hydrolysis mixture and recycled to the esterification of stage C.

8. The process according to claim 2, further comprising converting said crude acrylic acid to pure acrylic acid.

9. The process according to claim 1, wherein said cooling is performed so that said mixture is cooled to a temperature of from 120 to 180° C.

10. The process according to claim 9, wherein said cooling is performed in a spray cooler.

11. The process according to claim 1, wherein said cooling is performed in a spray cooler.

12. A process comprising:
    obtaining an acrylic acid gaseous reaction mixture by gas-phase oxidation;
    cooling said mixture in the presence of an inert high-boiling solvent;
    separating said mixture to provide a low-boiling fraction, a crude acrylic acid fraction, and a bottoms product, wherein said separating is conducted in a distillation column; and
    obtaining the crude acrylic acid via a sidestream takeoff of the distillation column.

13. The process according to claim 12, further comprising converting said crude acrylic acid to pure acrylic acid.

14. The process according to claim 12, wherein said cooling is performed so that said mixture is cooled to a temperature of from 120 to 180° C.

15. The process according to claim 14, wherein said cooling is performed in a spray cooler.

16. The process according to claim 12, wherein said cooling is performed in a spray cooler.

17. A process comprising:
    obtaining an acrylic acid gaseous reaction mixture by gas-phase oxidation;
    cooling said mixture in the presence of an inert high-boiling solvent;
    separating said mixture to provide a low-boiling fraction, a crude acrylic acid fraction, and a bottoms product, wherein said separating is conducted in a distillation column;
    obtaining the crude acrylic acid via a sidestream takeoff of the distillation column; and
    converting said crude acrylic acid to pure acrylic acid, said separating is conducted in a distillation column.

18. The process according to claim 17, wherein said cooling is performed so that said mixture is cooled to a temperature of from 120 to 180° C.

19. The process according to claim 18, wherein said cooling is performed in a spray cooler.

20. The process according to claim 19, wherein said cooling is performed in a spray cooler.

* * * * *